(12) United States Patent
Wendelburg et al.

(10) Patent No.: US 9,023,110 B2
(45) Date of Patent: May 5, 2015

(54) ELBOW JOINT PROSTHESIS AND METHOD FOR IMPLANTATION

(75) Inventors: Kirk Wendelburg, Hidden Hills, CA (US); Slobodan Tepic, Zurich (CH); Inja Tepic, Zurich (CH)

(73) Assignee: Kyon AG, Zurich (CH)

( * ) Notice: Subject to any disclaimer, the term of this patent is extended or adjusted under 35 U.S.C. 154(b) by 342 days.

(21) Appl. No.: 12/510,249

(22) Filed: Jul. 27, 2009

(65) Prior Publication Data

US 2012/0136450 A1 May 31, 2012

Related U.S. Application Data

(60) Provisional application No. 61/083,898, filed on Jul. 25, 2008.

(51) Int. Cl.
*A61F 2/38* (2006.01)
*A61F 2/30* (2006.01)

(52) U.S. Cl.
CPC ..... *A61F 2/3804* (2013.01); *A61F 2002/30205* (2013.01); *A61F 2002/30242* (2013.01); *A61F 2002/30286* (2013.01); *A61F 2002/30604* (2013.01); *A61F 2002/30879* (2013.01); *A61F 2002/3822* (2013.01); *A61F 2002/3827* (2013.01); *A61F 2002/3831* (2013.01); *A61F 2230/0063* (2013.01); *A61F 2230/0067* (2013.01); *A61F 2230/0071* (2013.01); *A61F 2310/00407* (2013.01)

(58) Field of Classification Search
CPC ................. A61F 2/38; A61F 2/3804; A61F 2002/30433; A61F 2/30; A61F 2220/0041; A61F 2/582; A61F 2002/2853; A61F 2002/2871
USPC ........................................... 623/20.11–20.13
See application file for complete search history.

(56) References Cited

U.S. PATENT DOCUMENTS 2,696,817 A * 12/1954 Prevo ........................ 623/20.12
3,708,805 A * 1/1973 Scales et al. ............... 623/20.12
4,206,517 A * 6/1980 Pappas et al. .............. 623/20.13

* cited by examiner

*Primary Examiner* — David Isabella
*Assistant Examiner* — Ann Schillinger
(74) *Attorney, Agent, or Firm* — Occhiuti & Rohlicek LLP

(57) ABSTRACT

A modular elbow prosthesis is disclosed, as well as a surgical approach and implantation technique, for using the prosthesis. The system is the first and only to allow for a, Biomechanically Anatomical, Nonconstrained, Compartmental (BANC) Elbow Arthroplasty. The modularity of the system allows it to be implanted as an unicompartmental or partial elbow replacement or a total elbow replacement. The modular elbow prosthesis for partial elbow replacement includes a cylindrical medial humeral component, a polyethylene ring thereon, and a semicircular medial ulnar component which mates with the polyethylene ring. Additionally, for total elbow replacement, the modular elbow prosthesis also includes a circular lateral humeral component, a polyethylene ring thereon, a semicircular lateral ulnar component, and a radial component. Implantation of the prosthesis is through a minimally invasive medial surgical approach with the aid of precision biomechanical guides. The application is well suited for canines, other quadrupeds, and people.

13 Claims, 12 Drawing Sheets

ELBOW JOINT PROSTHESIS AND METHOD FOR IMPLANTATION

CROSS REFERENCE TO RELATED APPLICATIONS

The present application claims priority to U.S. Provisional Application Ser. No. 61/083,898, filed Jul. 25, 2008.

BACKGROUND OF THE INVENTION

1. Field of the Invention

The present invention relates to elbow arthroplasty, particularly for canines. More particularly, it relates to a modular elbow replacement prosthesis and a procedure for implantation of the prosthesis.

2. Discussion of Related Art

The canine elbow is a complex hinge joint that moves about its center of rotation in a sagittal plane (sagittal range of motion arc). The distal humerus, proximal ulna, and proximal radius articulate at the elbow in all combinations. The humeroradial and humeroulnar articulations are the main load-supporting pairs. Axial load is transferred through both the humeroradial and humeroulnar articulations and the humeroulnar articulation is also loaded through the trochlear notch of the ulna and trochlea of the humerus by high levering forces exerted by the elbow extensor (triceps) muscles. The radius also rotates internally and externally within the radial notch of the ulna, independent from movement of the ulna. This independent rotation of the radial head allows for the normal pronation and supination that occurs during the canine gait.

Elbow dysplasia (specifically fragmented coronoid process) and the resulting osteoarthritis is the most common orthopedic problem in the canine forelimb. Arthrosis of the elbow in dogs is extremely debilitating with surgical and medical treatment frequently providing only partial and temporary success. Long term treatment success of fragmented coronoid process has been reported at less the 50% with medical management and less than 60% with surgical management. Standard treatment for severe arthrosis of the canine hip is the total hip arthroplasty. Total joint arthroplasty has been successfully performed in the canine coxofemoral joint with success rates reported up to 95%. Total elbow arthroplasty in the dog has not met with comparable success rates.

In dogs, elbow pathology originates on the medial (humeroulnar) compartment of the joint. Medial compartment cartilage erosion results from a fragmented coronoid process, incongruency, and osteochondrosis or osteochodritis desiccans. Severe medial compartment pathology frequently occurs without any significant lesions in the lateral (humeroradial) compartment. Unicompartmental knee replacements have been performed in people for decades. Published long-term clinical results of a unicompartmental knee demonstrated a 98% success rate at 10 years and 95% at 15 years and beyond. Unicompartmental knee patients also benefit from a less invasive procedure with a quicker recovery. There is a need for a unicompartmental elbow athroplasty that treats only the medial compartment of the elbow.

All prior attempts of elbow arthroplasty in the dog have been with systems that were constrained or semiconstrained, bicompartmental total elbow replacements. Unacceptable failure rates for total elbow arthroplasty are a result of treating the elbow as a unicompartmental joint with a constrained prosthesis. Constraint implies some type of mechanical link or coupling between the bones implanted with the prosthesis. Prior elbow replacements have not addressed the normal anatomical movement between the radius and ulna and have constrained this movement with the prosthesis. Ligaments and other soft tissue structures transfer stresses across the joint as they share in load transfer within the joint. Prosthesis constraint to another bone within the joint will transfer those stresses into the implant-bone interface, leading to early implant fixation failure. There is a need for a canine total elbow arthroplasty that recognizes the three compartments of the elbow joint—1) the humeroradial articulation, 2) the humeroulnar articulation, 3) the radioulnar articulation, and allows each to function naturally in a nonconstrained fashion.

Various prostheses and implantation processes have been proposed or used for partial or complete elbow replacement in humans, dogs, or other animals. Given the complex nature of the elbow joint, these prostheses are often complex having many interconnected parts. The implantation processes are similarly complex. They require precise removal of large portions of the bones at the elbow and precise placement of the various components of the prosthesis. Often, the implantation process requires removal of or damage to the ligaments of the elbow, which limits operation of the elbow following the replacement.

SUMMARY OF THE INVENTION

The present invention includes a modular prosthesis having limited components of simple geometries for either a partial or total elbow arthroplasty. The prosthesis provides a biomechanically anatomic, nonconstrained, and compartmental elbow replacement. According to one aspect of the invention, at first modular prosthesis is used for medial compartment replacement. According to another aspect of the invention, a second modular prosthesis is combined with the first modular prosthesis for a total joint replacement. The present invention also allows for a simplified implantation procedure.

According to one aspect of the invention, a unicompartmental partial elbow arthroplasty replaces only the medial (humeroulnar) compartment of the elbow joint using the first modular prosthesis. According to an aspect of the invention, the first modular prosthesis includes a humeral component, a polyethelene ring, and an ulna component. The humeral component is attached to the humerus. The ulna component has a half ring shape attached to the ulna. The polyelthene ring is positioned between the humeral component and the ulna component. According to another aspect of the invention, the humeral component replaces the medial condyle with a metal, bone replacing prosthesis. According to another aspect of the invention, the ulna component is a metal half-ring which replaces the medial coronoid of the ulna along with the medial half of the trochlear notch and anconeal process. According to another aspect of the invention, the humeral component acts as a ring carrier to hold the polyethylene ring in place. The polyethylene ring acts as a meniscus between the metal core of the medial humeral component and the metal ulnar component.

According to another aspect of the invention, the polyethylene ring has a conical outer surface. The ulnar component has a conical inner surface that matches and articulates with the outer surface of the polyethylene ring.

According to another aspect of the invention, the humeral component is compressed to the bone medially and laterally with a large transcondylar screw. The ulna component is compressed to the ulnar bone with radially positioned metal bone screws.

According to another aspect of the invention, the second modular prosthesis is used to replace the radial joint. The second modular prosthesis includes a humeral component, a ulnar component, a radial component, and a polyethelene ring. The humeral component replaces the articular surface and adjacent bone of the condyle lateral to the trochlea. The radial component attaches to the head of the radius. The ulnar component has half-ring shape attached to the ulna. According to an aspect of the invention, the ulnar component of the second modular prosthesis is offset from the ulnar component of the first modular prosthesis about the axis of rotation of the humeral component. According to another aspect of the invention, the humeral component acts as a ring carrier to hold the polyethylene ring in place. The polyethylene ring acts as a meniscus between the metal core of the lateral humeral component, the metal radial component, and the metal ulnar component. The second modular prosthesis allows for natural pronation and supination as the radius moves in its sagittal range of motion arc around the lateral humeral component.

According to another aspect of the invention, the polyethylene ring has a convex outer surface. The ulnar component of the second modular prosthesis a concave inner surface that matches and articulates with the outer surface of the polyethylene ring. Similarly, the radial component has a concave upper surface that also matches and articulates with the outer surface of the polyethylene ring.

According to another aspect of the invention, the humeral component is compressed to the bone medially and laterally with the same large transcondylar screw used to hold the humeral component of the first modular prosthesis. The ulna component is compressed to the ulnar bone with radially positioned metal bone screws. The radial component is compressed to the end of the radius with an axial metal bone screw.

According to another aspect of the invention, bony ingrowth and/or ongrowth is enhanced by providing bone facing surfaces with plasma coated titanium. Alternatively or additionally, ridges may be formed on the bone facing surfaces. According to another aspect of the invention, the ridges on the humeral components of the first and second modular prostheses are matched to prevent movement therebetween.

According to another aspect of the invention, a unique method of surgical approach is used for implanting both of the elbow prostheses. According to one aspect of the invention, the procedure includes a sagittal osteotomy of the medial epicondyle to access the medial elbow compartment while sparing the ligament. A transverse pin or drill bit is positioned through the center of rotation of the humeral condyles. The pin is used to precisely guide a circular mill removing the bone of the medial condyle and ulna. According to another aspect of the invention, a second circular mill, of a lesser diameter, is used to remove the bone of the articular surface of the lateral condyle and radial head.

According to another aspect of the invention, for partial elbow replacement, the ulna component of the first modular prosthesis is attached to the milled surface of the ulna. The humeral component, having the polyethelyene ring thereon, is positioned within the ulna component and held in place within an axial screw. According to another aspect of the invention, for total elbow replacement, the ulna component is attached to the milled surface of the ulna at an offset angle from the ulna component of the first modular prosthesis. The radial component is attached to the milled head of the radius. The humeral component is positioned within the ulna component and held in place, together with the humeral component of the first modular prosthesis, by a single, axial screw.

According to another aspect of the invention, the medial epicondyle is held onto the bone the humeral component with a screw that is threaded into the head of the large transcondylar screw. According to another aspect of the invention, fixation of the epicondyle to the humeral shaft is accomplished with a low profile locking plate.

According to another aspect of the invention, prior to commencing the implantation process, an osteotomy of the medial olecranon ridge for the insertion of the flexor carpi ulnaris muscle provides a minimally invasive approach to the medial elbow joint while protecting the ulnar nerve.

According to another aspect of the invention, a sagittal implantation board is used to rigidly mount the joint, to determine the sagittal plane, and to direct the cutting and drilling processes. The sagittal implantation board allows for rigid mounting of the humerus while allowing a normal range of motion in the elbow joint. A line between at least two points within the normal range of motion of the joint, together with the location of the joint, are used to establish the sagittal plane.

DETAILED DESCRIPTION

The present invention includes embodiments of a unique elbow prosthesis that replicates normal elbow biomechanics, that is totally nonconstrained between all three elbow compartments, that is modular allowing for a partial or total elbow replacement, and that is fully isometric allowing each component to be used in either right or left elbow. Elbow arthroplasty, in accordance with embodiments of the process and using the prostheses of the present invention, includes the partial elbow replacement and the total elbow replacement along with the instruments and the new and unique implantation technique. The implants and instrumentation are used but not limited to the treatment of canine elbow osteoarthritis. The embodied prosthesis, instruments and implantation technique are useful for treatment of other quadrupeds and humans.

Embodiments of the prosthesis of the present invention are illustrated herein in the replacement of all or a portion of a canine elbow. Of course, embodiments of the prosthesis may be used for elbows of other animals and humans. The structures of the elbow relevant to the replacement procedure and prosthesis are illustrated in FIGS. 1-5. These structures shown in these figures correspond to the structures shown in subsequent figures illustrating the procedure and implantation of the prosthesis.

Figure 1:
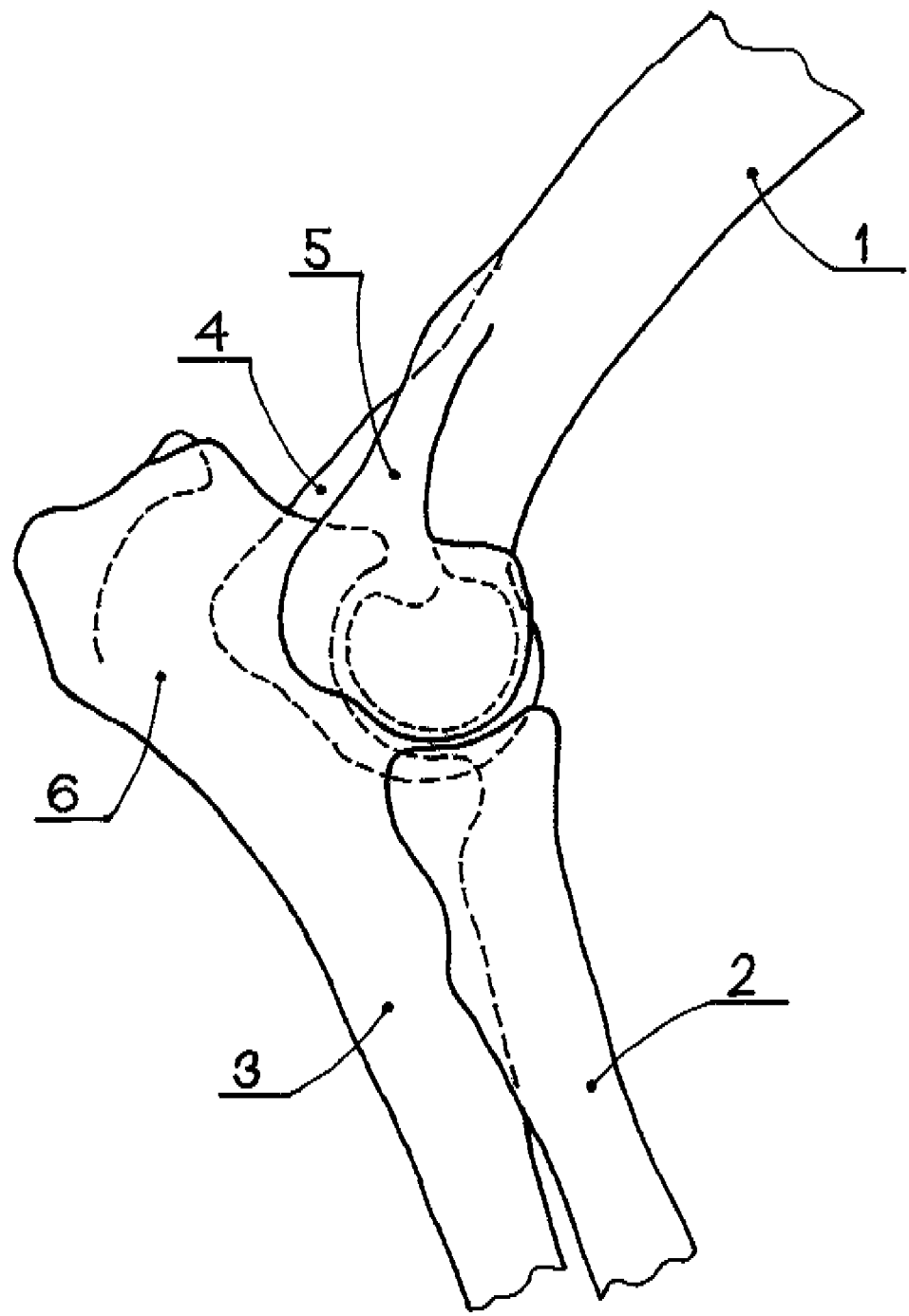
FIGS. 1-4 are views of a canine elbow for which the prosthesis of the present invention can be utilized.

FIG. 1 shows a latero-medial view of the right canine elbow. The humerus 1 articulates against the radius 2 on the lateral side of the joint and the ulna 3 on the medial side of the joint. The distal end of the humerus widens into the lateral 5 and medial 4 epicondyles. Proximally, the ulna extends past the joint into the olecranon 6.

Figure 2:
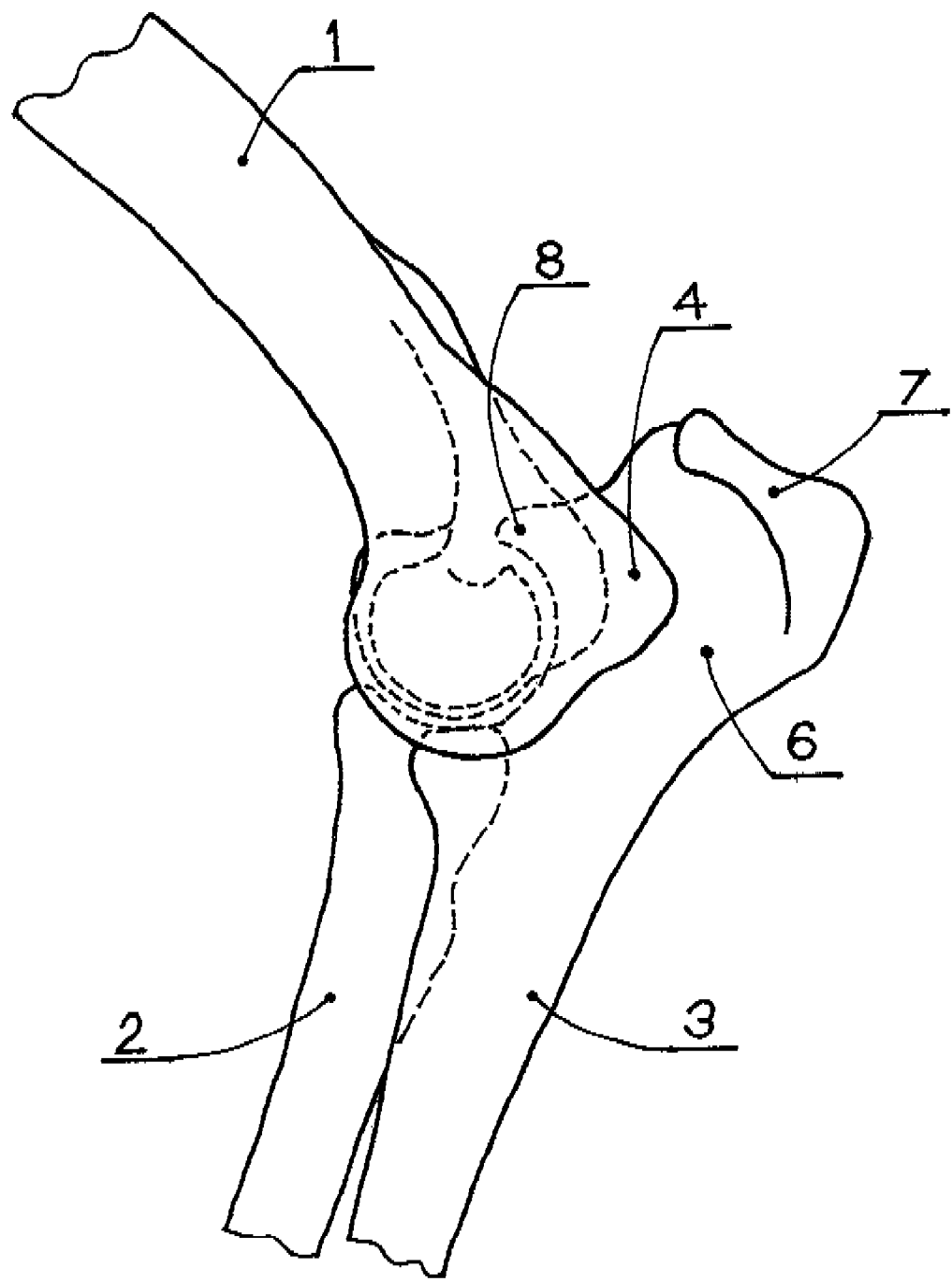

FIG. 2 shows a medio-lateral view of the right canine elbow. The medial ridge 7 of the olecranon 6 is the insertion site of the flexor carpi ulnaris muscle. The semi-circular articular surface of the ulna ends proximally with the anconeal process 8.

Figure 3:
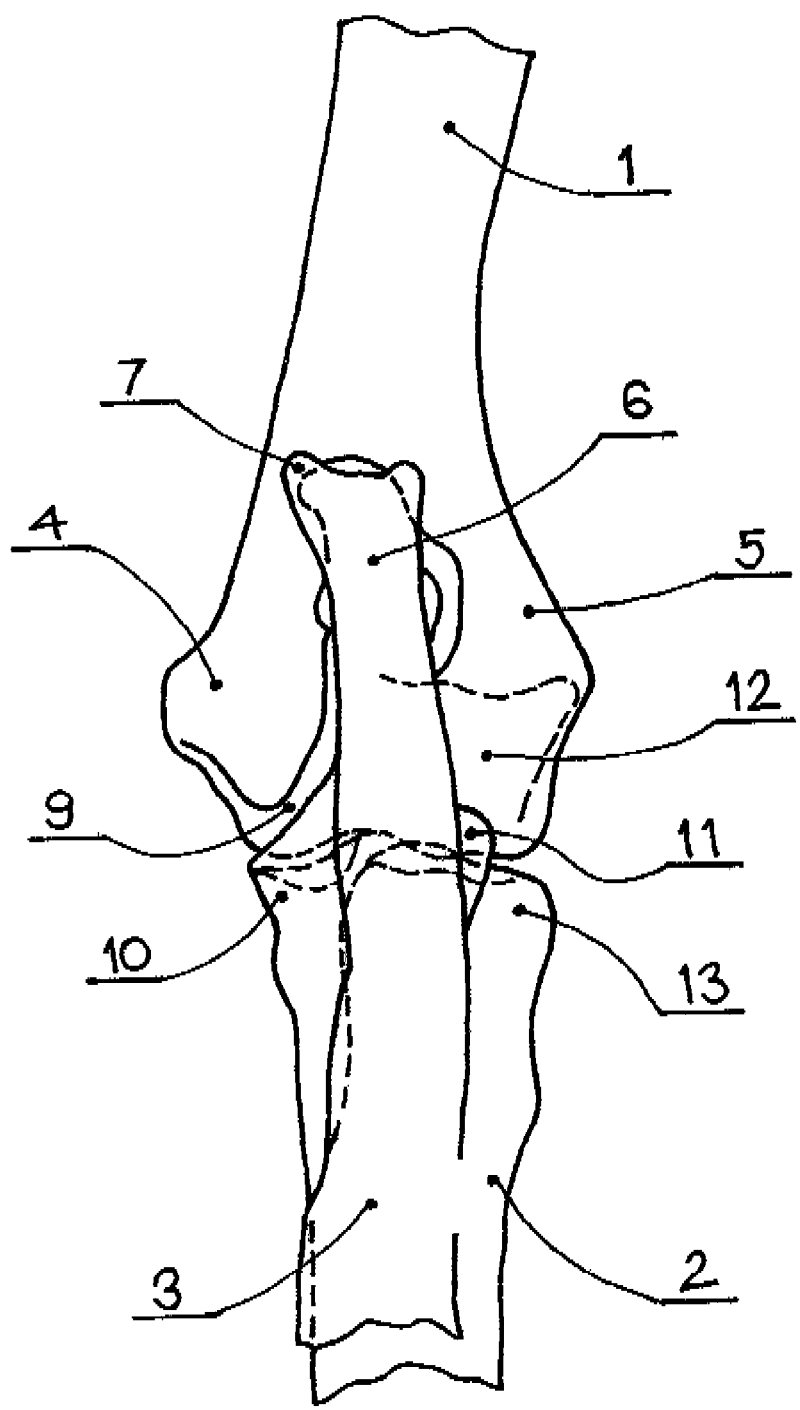

FIG. 3 shows a caudo-cranial view of the right canine elbow. The medial humeral condyle 9 articulates against the ulna—the most medial aspect of which is the medial coronoid process 10; the most lateral aspect is the lateral coronoid process 11 which articulates against the lateral humeral condyle 12. The lateral humeral condyle 12 also articulates against the radial head 13 of the radius 2.

Figure 4:
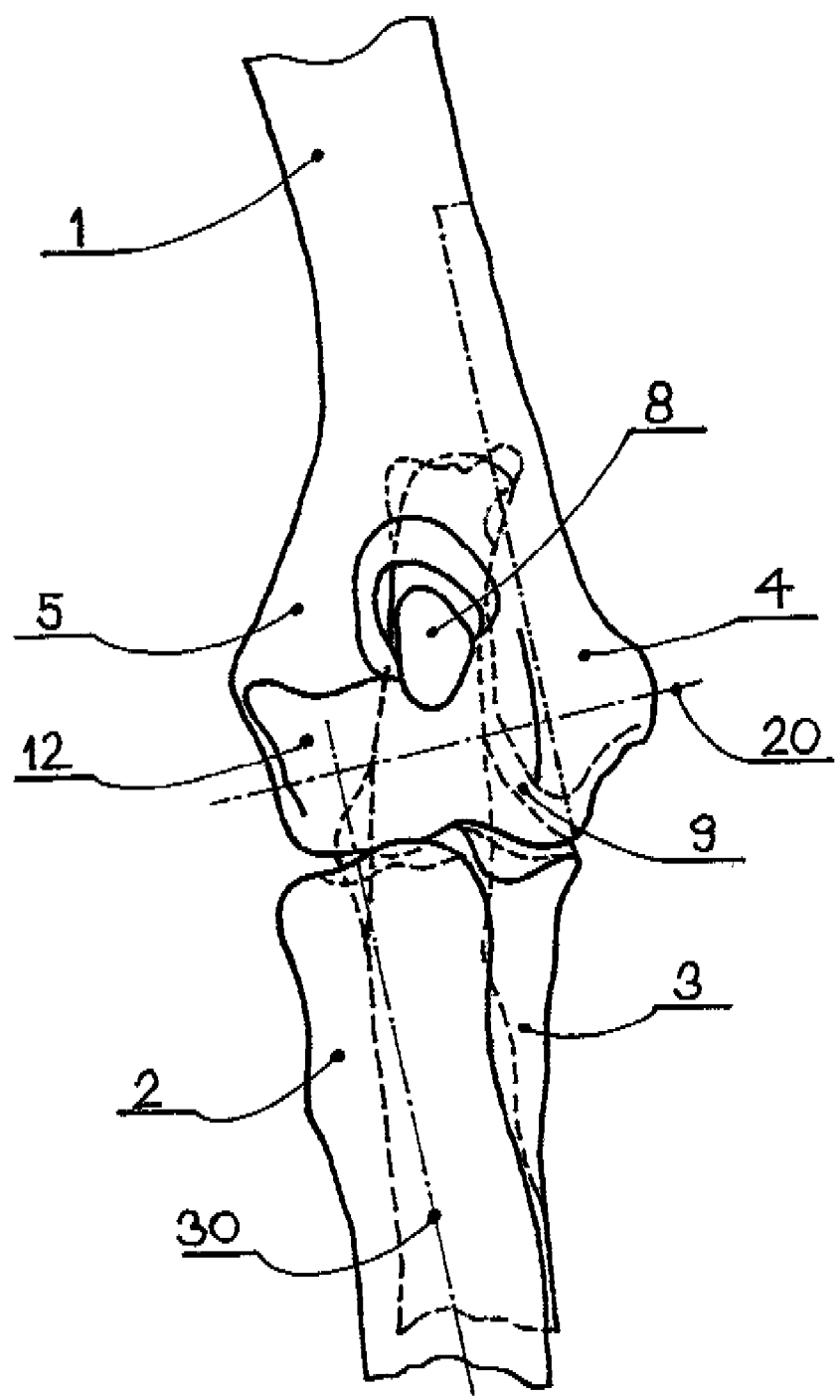

FIG. 4 shows a cranio-caudal view of the right canine elbow. The flexion-extansion movement of the distal limb (comprising the ulna, 3, and the radius, 2) with respect to the humerus 1 is closely approximated by a rotation around a fixed axis 20, i.e. the joint between the humerus and the distal limb is basically a hinge joint. Axial rotation between the humerus and the ulna is minimal. However, the radius has a considerable range of freedom to rotate against the humerus—and consequently the ulna—approximately around its long axis 30. This allows for the pronation/supination of the distal limb.

Figure 5:
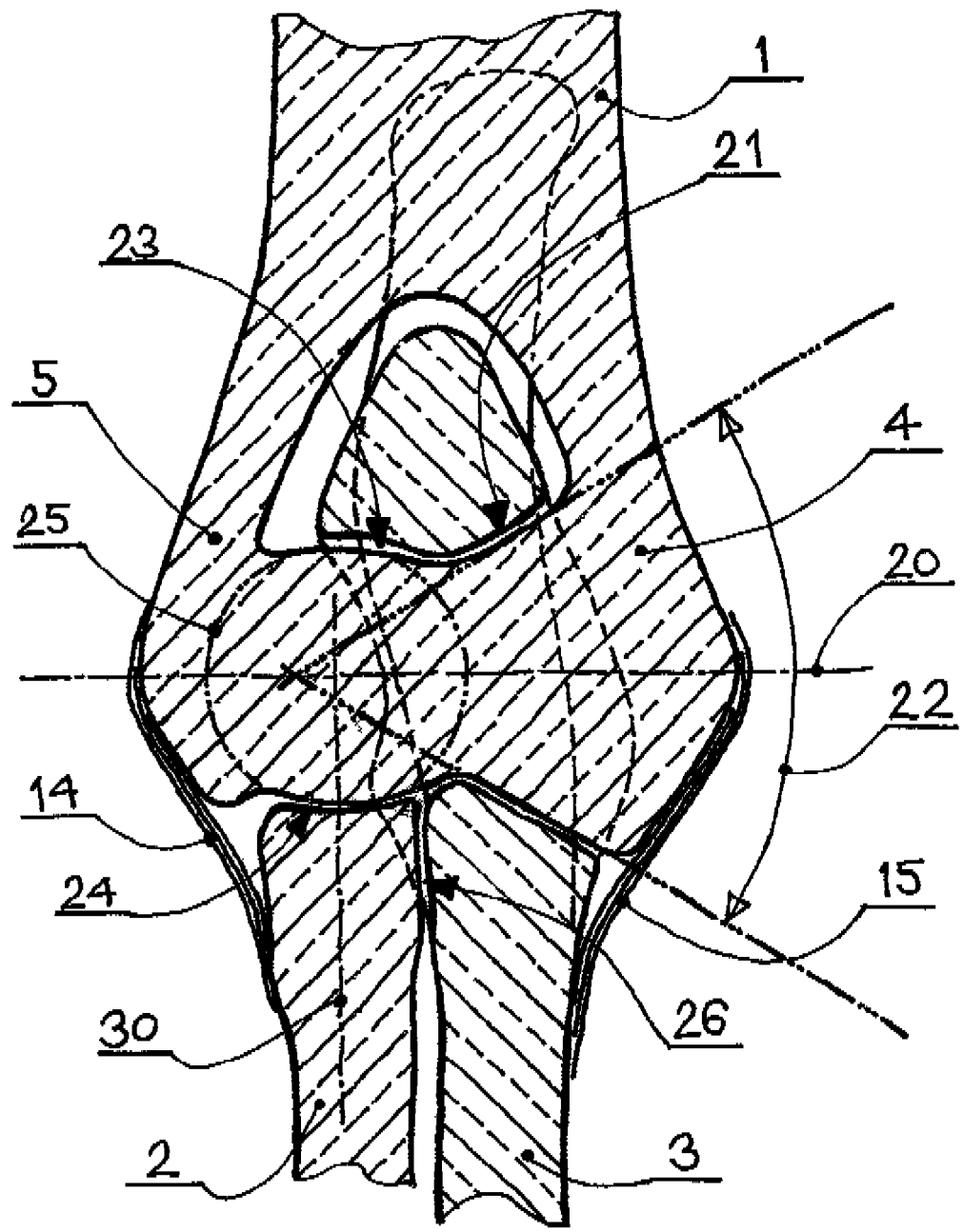
FIG. 5 is a cross sectional view of an elbow showing the structures to which the prosthesis of the present invention are applicable.

FIG. 5 is a cross sectional view of the elbow in approximately the frontal plane. The articulating surface 21 between the medial humerus and the medial ulna is closely approximated by a cone 22 centered on the axis 20. The shape of the lateral compartment articulations is nearly spherical 25 for both the humeroulnar articulation 23 and for the humeroradial articulation 24. The radioulnar articulation 26 remains partially intact in this procedure—its shape is cylindrical. Rotation of the radius 2 around its axis 30 does not disturb the congruency of either the humeroradial or the radioulnar articulation. The joint is stabilized by a ligament 14 crossing from humerus 1 to radius 2 on the lateral side and by a ligament 15 crossing from humerus 1 to ulna 3 on the medial side. The surgical approach and insertion of the prosthetic components are performed without disrupting these important ligaments.

Figure 10:
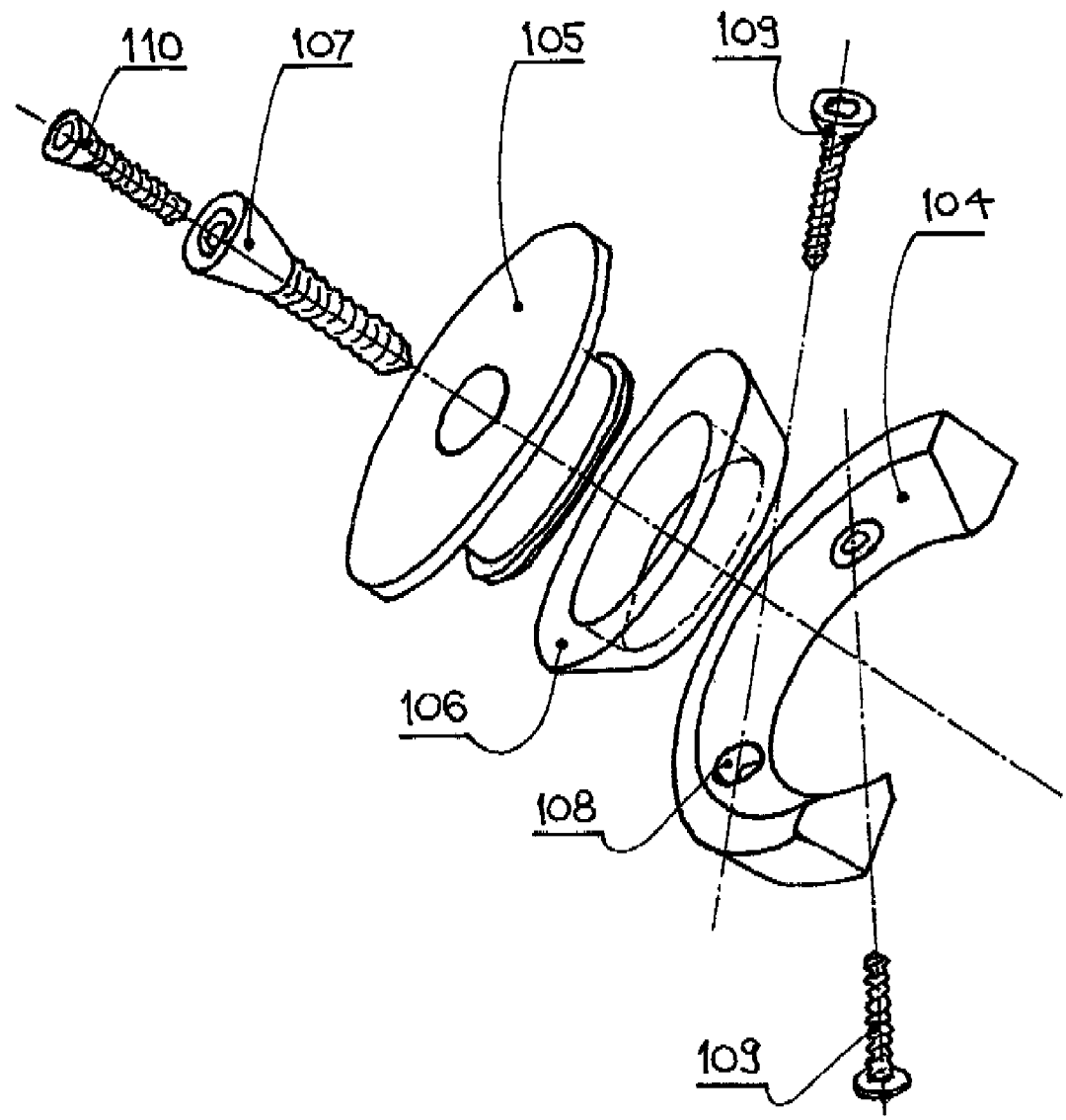
FIG. 10 is an exploded, perspective view of the components of an elbow prosthesis according to an embodiment of the present invention for total elbow replacement.
Figure 11:
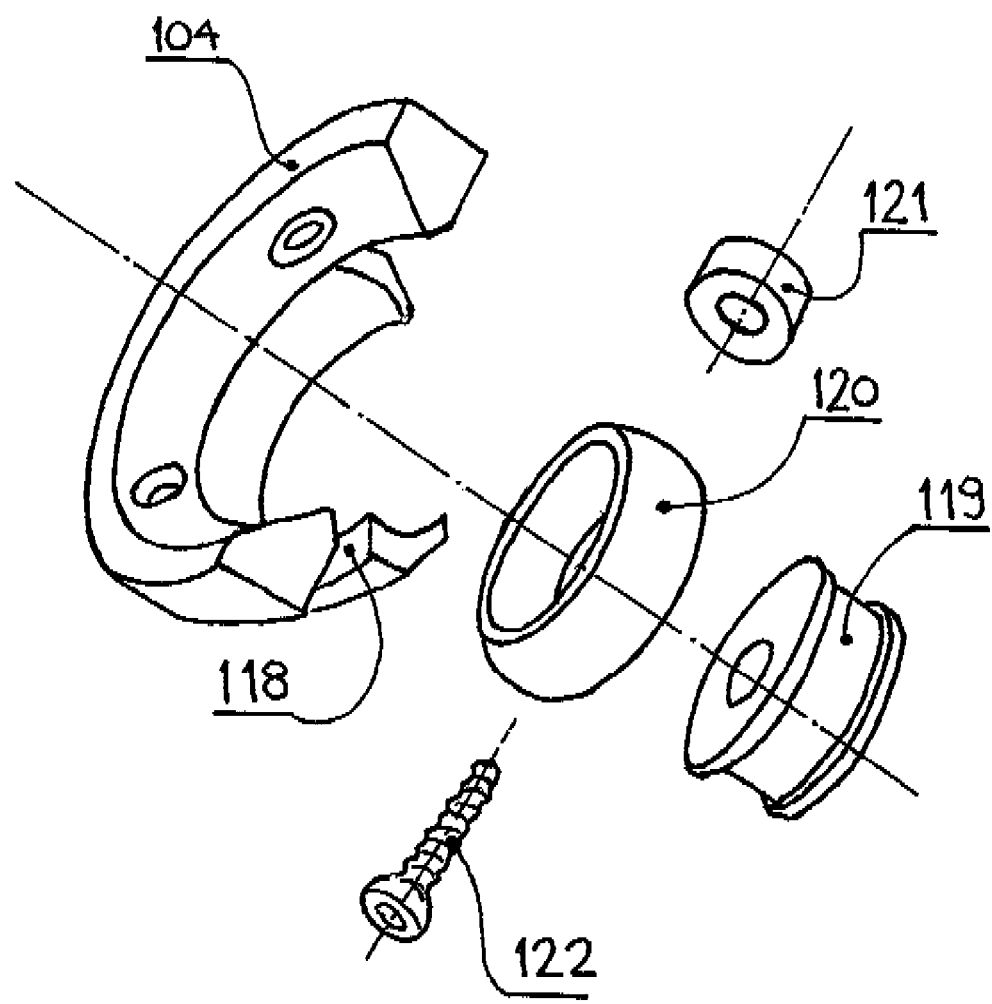
FIG. 11 is an exploded, perspective view of the components of an elbow prosthesis according to an embodiment of the present invention for partial elbow replacement.

An embodiment of the modular prosthesis is illustrated in FIGS. 10 and 11. FIG. 10 illustrates a first set of components for a partial elbow replacement. FIG. 11 illustrates a second set of components, which are used with the first set of components for a total elbow replacement. The modular prosthesis, as illustrated in the embodiment of FIGS. 10 and 11, includes a medial humeral component 105, a medial polyethylene ring 106, a medial ulnar component 104, a lateral humeral component 119, a lateral polyethylene ring 120, a lateral ulnar component 118, and a radial component 121.

Figure 12:
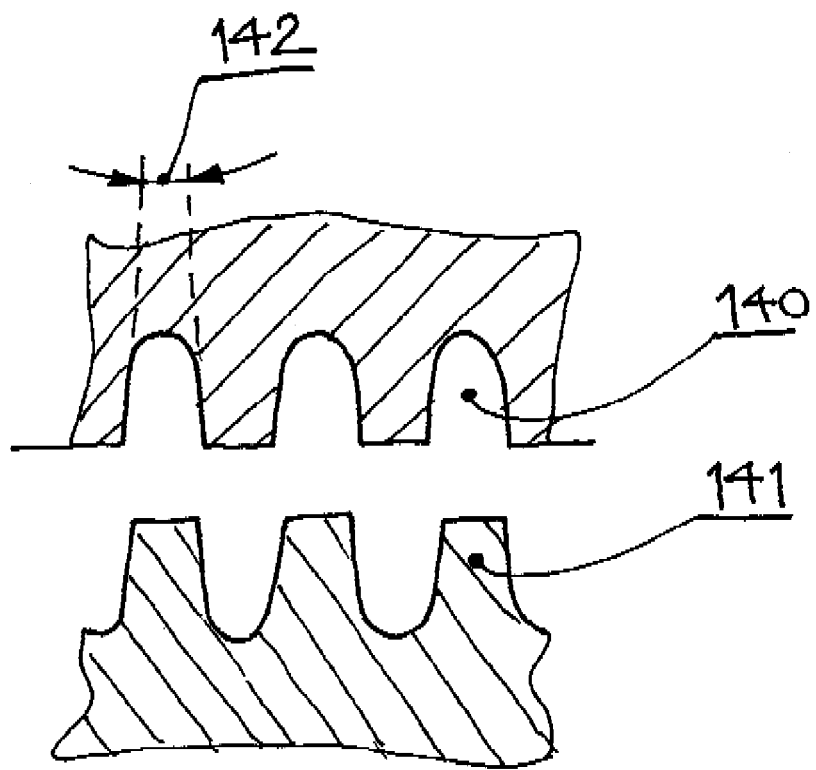
FIG. 12 illustrates ridges on a prosthesis according to an embodiment of the present invention.

The medial humeral component 105 is cylindrical in shape. It includes a central hole that transverses the implant from medial to lateral. The hole is countersunk medially for the transcondylar 4.0 mm bone screw 107. The medial and lateral end plates of the medial humeral component 105 of a larger diameter than the central portion. Preferably, the medial end plate is of a larger diameter than the lateral end plate. The end plates are shaped and/or coated for bone ingrowth or ongrowth. For example, they may be plasma coated. Alternatively, they may have surface structures, such as a set of ridges as illustrated in FIG. 12. Of course, plasma coating may also be used in conjunction with a surface structure.

The medial polyethylene ring 106 is positioned on the medial humeral component 105. The medial polyethylene ring 106 is circular in shape. It has a central bore of approximately the diameter of the central portion of the medial humeral component 105. The medial polyethylene ring 106 may rotate about the central portion of the medial humeral component. The outer surface of the medial polyethylene ring 106 is conical. The width of the medial polyethylene ring 106 is substantially the distance between the end plates of the medial humeral component 105. The end plates of the medial humeral component 105 are smaller, preferably about 1 mm, than the respective outer radii of the polyethylene member.

The medial ulnar component 104 is semicircular in shape. It has a polished concave metal articular surface that is complimentary to the conical polyethylene ring 106. The articular surface has two countersunk screw holes for the insertion of bone screws used to compress and rigidly fix the component to the underlying bone bed. The outer semicircular and flat lateral surfaces may have circular ridges and/or a porous material for bone ingrowth and/or ongrowth. The edge of the medial ulnar component 104 between the lateral (internal) aspect of the articular surface and the flat lateral bony-ingrowth surface may have a bevel, such as 1 mm, to prevent contact with the adjacent articular cartilage of the humerus.

The lateral components of the prosthesis are similar in material and design to the medial components. The lateral humeral component 119 is cylindrical with a central bore. It includes end plates of slightly larger diameter than a central portion. However, for the lateral humeral component 119, the end plate diameters are substantially identical. In an embodiment of the invention, the diameters of the end plates of the lateral humeral component 119 are approximately the same as the smaller end plate of the medial humeral component 105. In an embodiment of the invention, the inner endplate is countersunk and is formed or coated for bone ingrowth and/or ongrowth. The outer endplate may include ridges. The ridges in the outer endplate may be formed to mate (as illustrated in FIG. 12) with ridges on the endplate of the medial humeral component 105. In this manner, the two humeral components are firmly joined together.

The lateral polyethylene ring 120 fits around the central portion of the lateral humeral component 119. As with the medial polyethylene ring 106, the lateral polyethylene ring 120 may rotate on the lateral humeral component 119. The end plates of the lateral humeral component 119 are preferably smaller than the sides of the lateral polyethylene ring 120. The outer diameter of lateral polyethylene ring 120 is prolate spheroid (barrel shaped).

The lateral ulnar component 118 is semicircular. It has a smaller outer radius, such as 2 mm less, than the medial ulnar component 104. The internal medial radius of the component has an equal inner radius to the complimentary medial ulnar component with the same 1 mm bevel on the internal edge. The articular surface is polished and concave. It is complimentary to the prolate spheroid outer surface of the lateral polyethylene ring 120. The medial and convex outer surfaces of the lateral ulnar components are bony-ingrowth and have circular ridges to aid in stability and ingrowth. The ends of the semicircular lateral component are tapered toward the inner or medial aspect of the prosthesis.

The radial component 121 has a surface to match the milled radial head bone. It has a polished upper surface which is concave and complementary with the outer surface of the lateral polyethylene ring 120. It is attached to the head of the radius 2 by a screw 122.

Figure 9:
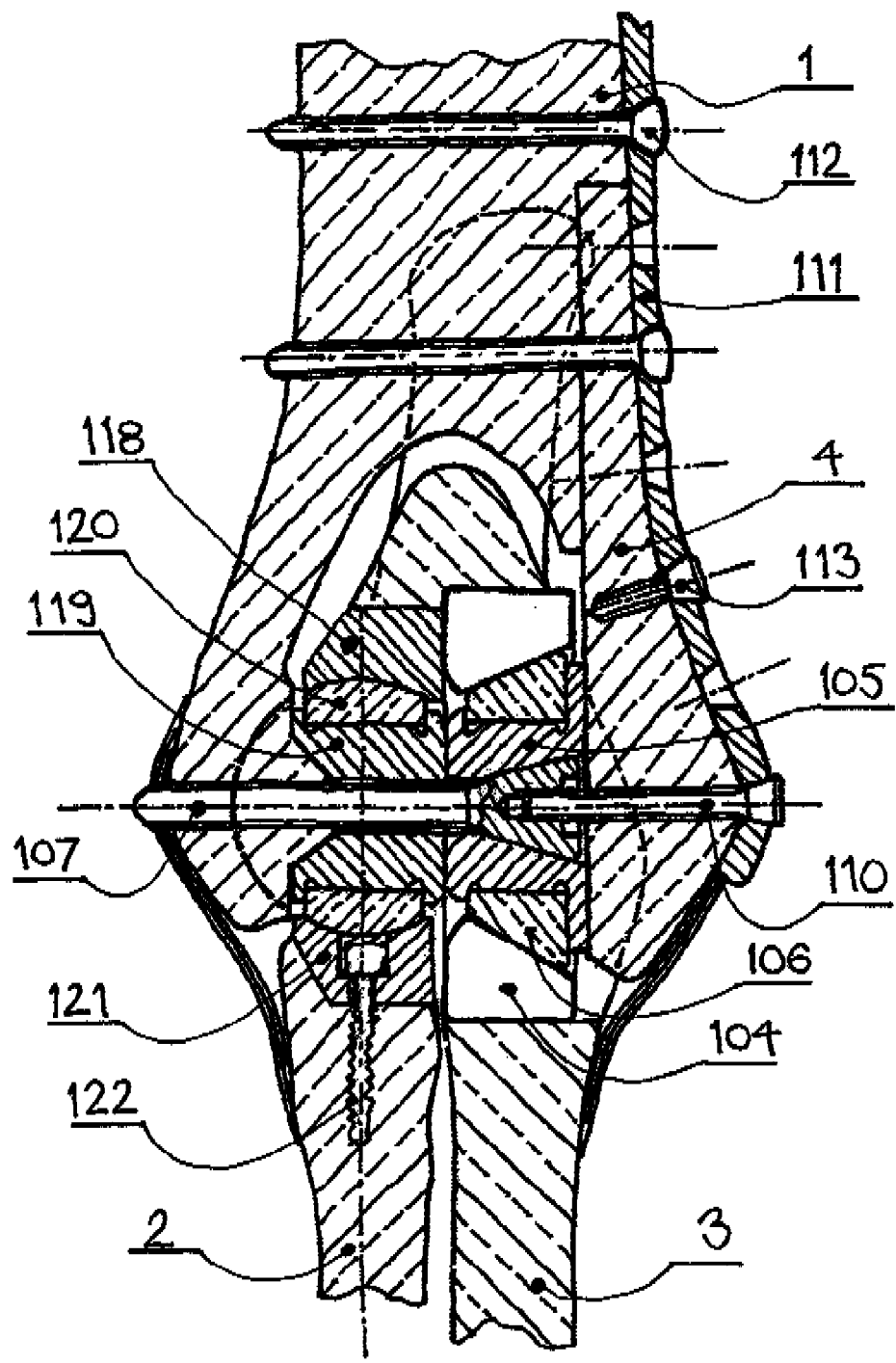
FIG. 9 is a cross sectional view of an elbow having a prosthesis according to an embodiment of the present invention.

FIG. 9 illustrates the components of a prosthesis within a elbow according to an embodiment of the invention. The prosthesis is positioned within a hole milled in the elbow. The lateral ulnar component 118 and medial ulnar component 104 are attached to the ulna 3 within respective milled holes. Bone screws, not shown, are used to attach these components 104, 118 to the ulna 3. The bone screws are arranged radially with respect to the semicircular components. The radial component 121 is attached to the head of the radius 2 using a bone screw 122. The lateral humeral component 119 and medial humeral component 105 are attached to the humerus 1 with a single transcondylar bone screw 107. The medial humeral component 105 completely replaces the removed bone of the medial condyle.

A unique technical aspect of the prosthesis of the present invention is the reversal of the common use of materials for the concave and convex side of the articulation. In all commercially available prosthesis using soft-hard combination, the soft side polyethylene (usually produced from Ultra High Molecular Weight Polyethylene—UHMWPE) is placed on the concave component. In the prosthesis of this invention, the concave side is polished metal and the polyethylene member is placed on the convex, humeral side of the joint. This allows for the simple conical cylinder-ring shape of the polyethylene member which articulates with both the metal humeral condylar core and the metal ulnar or radial components. This meniscus-type configuration of the polyethylene ring leads to reduced polyethylene wear since movement is shared between the fully congruent articulation of the polyethylene ring and its metal carrier and the outer articulation with the ulnar or radial components.

Figure 7:
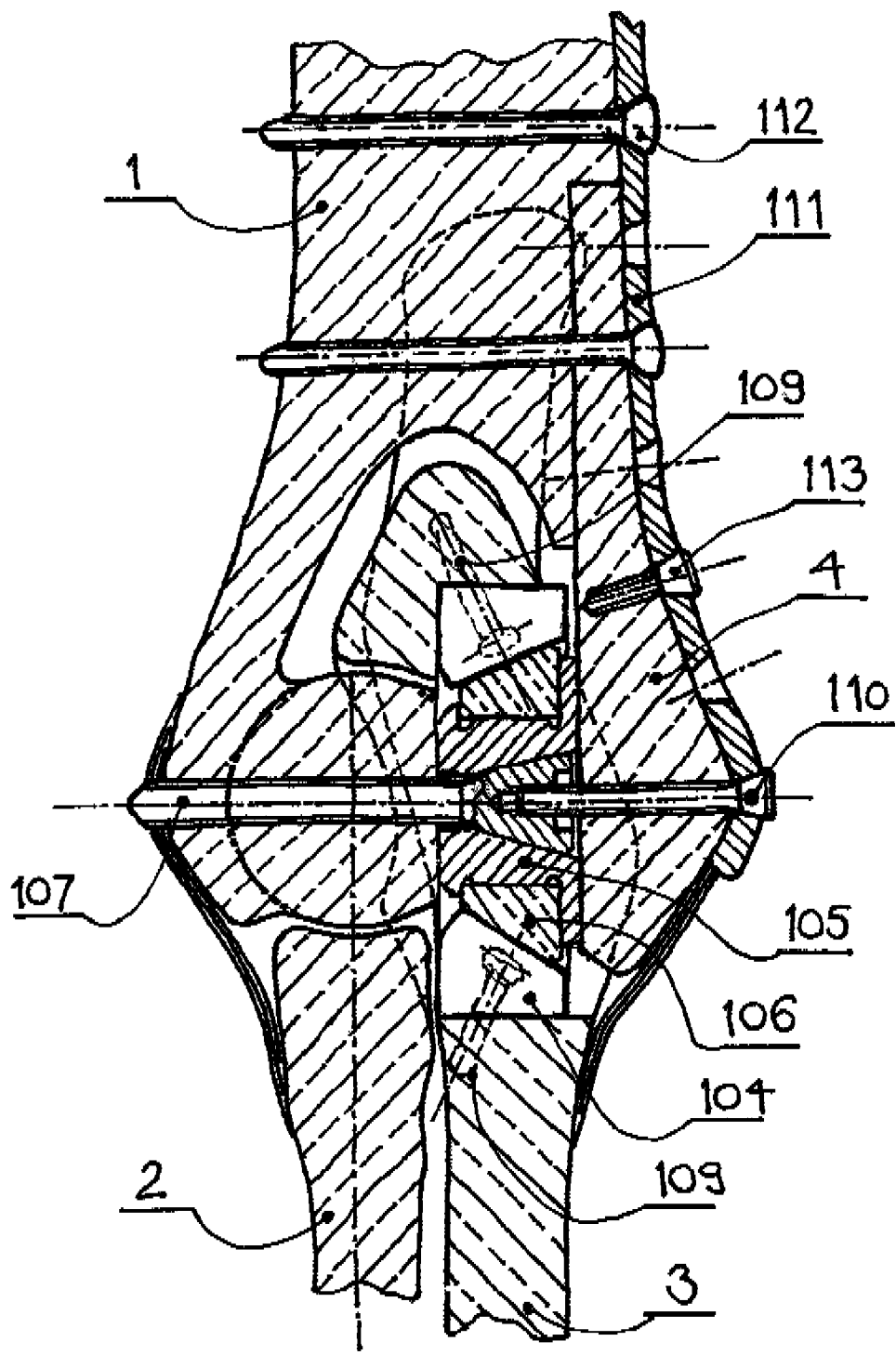
FIG. 7 is a cross sectional view of an elbow having a prosthesis according to an embodiment of the present invention.

A partial elbow replacement is accomplished using only the medial components of the prosthesis, including the medial humeral component 105, the medial polyethylene ring 106 and the medial ulnar component 104. The components for the partial elbow replacement are illustrated in FIG. 11. The partial elbow replacement is illustrated in FIG. 7. The prosthesis is positioned within a hole milled in the elbow. However, the milled hole for the partial elbow replacement is not as extensive as for a total elbow replacement. The medial ulnar component 104 is attached to the ulna 3 within the milled hole. Bone screws 108, 109 are used to attach the medial ulnar component 104 to the ulna 3. The bone screws are arranged radially with respect to the semicircular component. The medial humeral component 105 is attached to the humerus 1 with a transcondylar bone screw 107. The same bone screw 107 used for the total elbow replacement is used for the partial elbow replacement. However, it extends through additional unmilled bone in the humerus 1 instead of the lateral humeral component 119. The radius 2 is unaffected by the partial elbow replacement.

The materials and structures of the prosthesis described above are merely embodiments of the invention. Preferably, the joint includes a polyethylene—polished metal junction. In the embodiment disclosed above, that junction is between a polyethylene ring on a humeral component and a polished ulnar or radial component. Alternatively, the ulnar and/or radial component could have a polyethylene surface which interacts with a polished metal surface of the humeral component. Additionally, other metals or non-metals may be used for various components.

In another embodiment, the radial component 121 has two parts—a metal base and a metal articular meniscus. In this embodiment, the metal base has an outer (distal) convex cylindrical surface that is the same radius as the outer convex surface lateral ulnar component and the underlying milled bone surface of the radius. The lateral surface of the metal base is flat to compress against the flat lateral surface of milled radial head bone. The proximal to distal outer appearance of the metal base is somewhat like a D in shape. The outside medial to lateral width of the metal base is one millimeter less than the diameter of the lateral humeral component to allow space for unhindered radial head rotation adjacent to the medial ulnar component. The flat lateral surface and the outer, convex, distal surface of the metal base have porous bony ingrowth ridged surfaces. The metal base has a raised vertical metal wall that contains the cylindrical insert of the metal meniscus. The polished convex cylindrical surface of the meniscus is complimentary to the polished inside surface of the vertical walls of the base. The lower (distal) surface of the metal meniscus is a polished flat articular surface that is complimentary to the proximal round articular surface of the metal base. The proximal surface of the metal meniscus has an elliptic paraboloid shaped articulating concave surface that is complimentary with the prolate spheroid polyethylene of the lateral condyle component. It snap fits into the metal base to allow rotational freedom while the radius pronates and supinates within the radial fossa of the ulna. The concaved elliptical paraboloid articular surface of the radial meniscus remains in absolute congruency with the lateral humeral component articular surface throughout the sagittal range of motion arc of the radius. The humeral-radius congruency is maintained throughout the entire range of motion since rotation motions occur at the radius base-meniscus junction. This configuration eliminates constraint between the radial and ulnar components and the radial and lateral humeral components.

A new and minimally invasive technique can be used with the prosthesis of the present invention to replace just the medial or total elbow compartments. Of course, other techniques or procedures may be used to implant the prosthesis of the present invention.

Preoperatively, the patient is evaluated with x-ray, CT, or arthroscopy in order to prepare for the procedure. The prosthesis may be of various sizes to accommodate different elbow dimensions. Using the obtained images of the patient, the elbow is measured using a mylar template or commercially available computer programs to determine the appropriate implant size. Sizing of the implant is also easily performed intraoperatively in connection with the procedure.

The patient is positioned on a sagittal positioning board with the medial surface of the limb facing upward. The sagittal positioning board is designed to identify the sagittal plane for the limb. The procedure, as described below, includes removing a portion of the bones parallel to the sagittal plane and milling bones perpendicular to the sagittal plane. While the sagittal positioning board described herein may be used to determine the sagittal plane and to properly position the tools for completing the procedures, any positioning board and/or tools may be used. The sagittal positioning board includes three partially threaded pins for insertion in the bones of the arm. The pins are connectable to fixation pins to hold the arm above the level of the sagittal positioning board.

Partially threaded pins is inserted into the cranial surface of the proximal and mid-shaft humerus. The pins are inserted in the estimated sagittal plane of the humerus. Another partially threaded pin is inserted into the distal radius, just lateral to the extensor carpi radialis tendon. This pin is also inserted in the estimated sagittal plane of the radius.

The patient's humerus is then fixed to the sagittal positioning board with fixation pins and torque free clamps, with the range of motion arc of the radius near parallel to the board. The antebrachium (limb distal to the elbow) is moved in its normal range of motion to establish the sagittal range of motion arc. With the elbow flexed to an angle of approximately 40 to 60 degrees, a first sagittal fixation pin and clamp are inserted into the sagittal positioning board. The clamp is fixed to the sagittal fixation pin at the level of the distal radial sagittal arc pin. The elbow is extended to an angle of approximately 140 to 160 degrees and a second sagittal fixation pin is inserted into the sagittal positioning board with the clamp again at the level of the distal radius sagittal arc pin. The positioning pins and clamps represent two points on the sagittal plane. The joint itself provides the third point to represent the plane. Thus, the tools can be properly positioned relative to the sagittal plane.

According to an embodiment of the present invention, a tool support may be attached to the sagittal positioning board connected to the fixation pins and clamps in order to operate within the desired plane. A sagittal line guide rod is inserted into the clamps and secured. A sagittal saw guide may be placed on the line guide rod for guiding a saw for cutting bone parallel to the sagittal plane. Similarly, a transverse drill guide may be laced on the line guide rod for guiding a drill perpendicular to the sagittal plane.

A sagittal fixation pin and clamp are used to firmly attach the radius pin to the sagittal positioning board to stabilize it in the extended position of its natural sagittal range of motion arc. A sagittal fixation pin and clamp are inserted into the sagittal fixation board caudal to the ulna at the level of the mid-diaphysis. A smooth k-wire is inserted in a caudal to cranial direction through the radius and ulna using the torque free clamp as a drill guide to further stabilize the antebrachium. This clamp is tightened for rigid fixation of the brachium and antebrachium.

Figure 6:
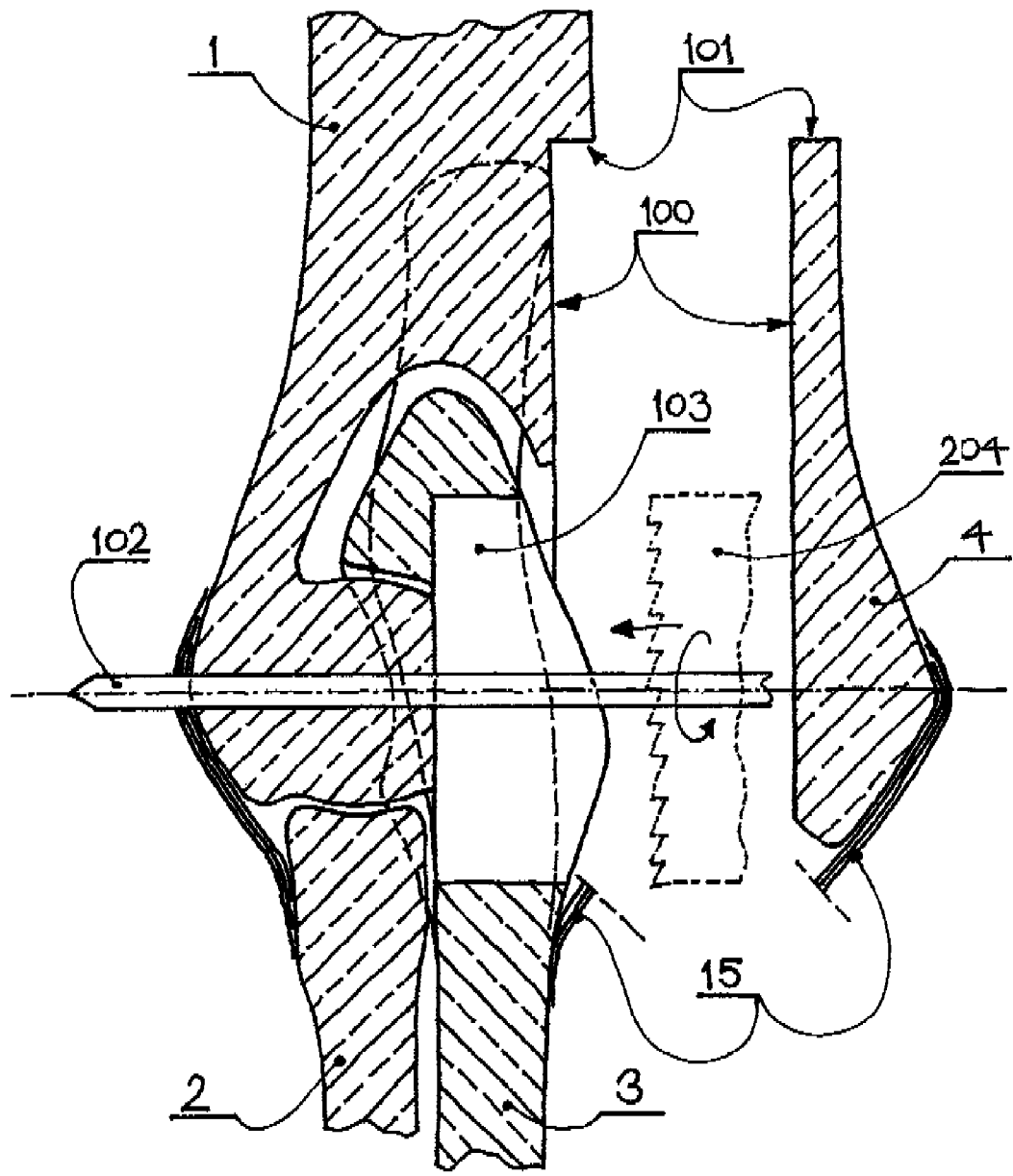
FIG. 6 is a cross sectional view of an elbow during a procedure for implanting a prosthesis according to an embodiment of the present invention.

Once the humerus, radius, ulna and sagittal line guide fixation pins and clamps are rigidly fixed to the sagittal positioning board a medial skin incision is made centered over the elbow joint. A sharp incision is made over the caudal ulna at the caudal insertion of the flexor carpi ulnaris. The proximal 20% of the muscle is elevated off the ulna and a sagittal osteotomy of the medial olecranon ridge for the proximal origin of this muscle is performed. The osteotomy and elevation of the flexor carpi ulnaris allows cranial retraction of the muscle which protects the ulnar nerve and exposes the medial elbow joint and epicondyle. A saw is used to accurately perform a sagittal osteotomy of the medial epicondyle. This sagittal osteotomy is performed to expose the medial elbow compartment while sparing ligaments, muscles and other soft tissues. The removal of the medial epicondyle 4 by the sagittal osteomtomy 100 is illustrated in FIG. 6. A transverse cut 101 above the ulna may be made to limit the amount of bone removed. The medial epicondyle 4 is reflected in a craniodistal direction. The medial locater ligament remains attached and unaffected by this procedure.

A high speed burr and ronguers are used to remove medial condylar bone to the level of the trochlea and medial boarder of the radius. After visualizing the circular articular surface of the condylar bone at the level of the trochlea, a guide pin 102 is positioned in the center of the trochlear circle (center of rotation). The guide pin may be inserted using a transverse drill with a 3.2 drill bit. A drill guide may be attached to the sagittal guide line to provide accurate positioning of the drill perpendicular to the sagittal plane. The 3.2 drill bit is inserted through the condylar bone and into the sagittal positioning board to hold it in place. The drill bit is removed from the drill. The 3.2 drill bit is now in the precise transverse axis of the elbow joint and is perpendicular to the sagittal range of motion arc of the elbow joint. The drill bit now becomes the guide pin 102 for the precise center of rotation guide of the elbow joint and is used to perform all further bone milling with exacting accuracy.

A medial compartment reaming or milling tool 104 is now used to remove medial ulna and humeral condylar bone to the level of the central trochlea. The joint surfaces remain congruent throughout the milling process. A very small amount of cranial radius 2 will be removed when the milling is complete. Throughout the milling process, the collateral and annular ligaments, joint capsule and other soft tissue structures are protected by gentle retraction.

Implant size is inspected, with the lateral polyethylene diameter of the medial humeral condyle component equal to the condylar articular cartilage diameter at the milled bone bed.

If a partial elbow arthroplasty is elected, the guide pin 102 is removed and the medial components are implanted into the bone bed, as illustrated in FIG. 7. The medial ulnar component 104 is firmly placed into the milled bone bed 103 of the ulna 3. The cranial aspect of the implant should be even to the cranial aspect of the radius. While compressing the implant to the bone bed, two screw holes are drilled and bone screws 108, 109 are placed to rigidly fix and compress the medial ulnar component 104 to the bone bed. The screw length for the transcondylar screw 107 is measured. The medial humeral component 105, having the medial polyethylene ring 106 thereon, is then placed on the milled surface of the humeral condyle 103. The 4.0 bone screw 107 is inserted into the center of rotation hole and tightened to compress the medial humeral condyle component to the condylar bone.

Once all components of the prosthesis are implanted, range of motion and congruency are confirmed. A medial epicondyle positioning screw is then inserted into the internally threaded 4.0 mm transcondylar screw head. The medial epicondyle 4 is anatomically reduced to the osteotomy site and lightly tapped or pressed onto the point of the positioning screw. The epicondyle 4 is lifted and over drilled from the inside-out with a 3.2 drill bit. The positioning screw is removed and the epicondyle 4 is reduced while lining-up the predrilled bone hole with the internal threaded hole of the 4.0 transcondylar screw using a 0.045 k-wire. The epicondyle 4 is held reduced while a malleable plate template is placed over the pin onto the epicondyle and medial humeral bone. The plate 112 used to repair the medial condylar osteotomy is a locking screw technology (ALPS). The epicondyle screw 110 is lagged through the plate 111 and over-drilled bone hole of the medial epicondyle 4 to compress the plate and bone against the bony ingrowth medial surface of the medial humeral component 105. A 2.4 mm plate screw 112 is inserted into a proximal plate screw hole in normal fashion. The remaining screws 113 in the epicondyle and humeral shaft are inserted under locking screw technique.

Figure 8:
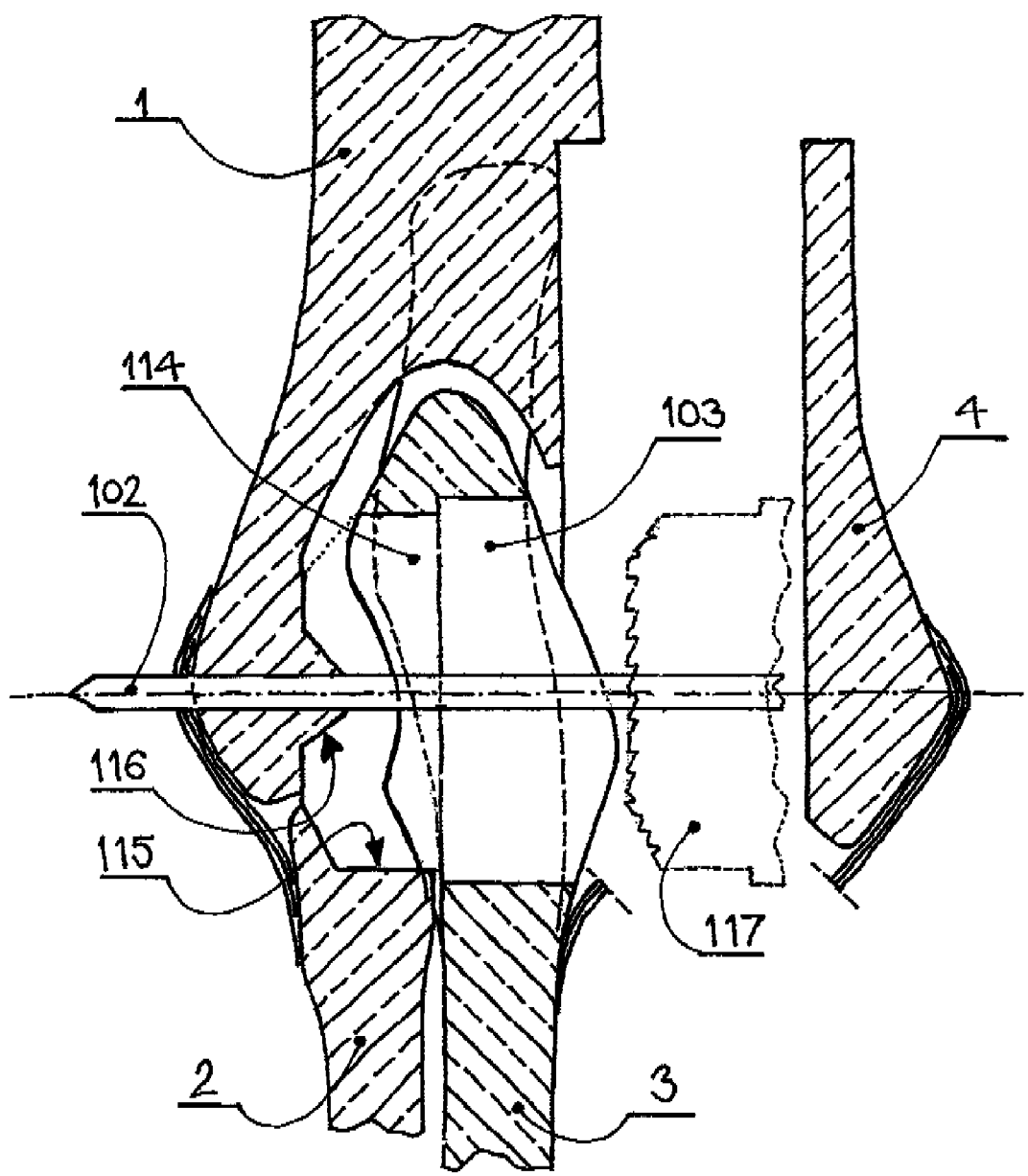
FIG. 8 is a cross sectional view of an elbow during a procedure for implanting a prosthesis according to an embodiment of the present invention.

If a total elbow arthroplasy is elected, either preoperative or intraoperative, the guide pin 102 is left in place after milling of the medial elbow compartment 103. The guide pin 102 acts as the center of rotation guide for precise milling of the lateral elbow compartment 114, as illustrated in FIG. 8. A lateral compartment milling guide is placed on the guide pin 102. The lateral compartment mill tool 117 is placed through the lateral compartment milling guide used in a high speed bur device to remove the cartilage and bone of the lateral compartment. The outer radius of the milled lateral compartment 114 is 2 or 3 millimeters smaller than the reamed radius of the medial compartment 103. The internal radius of the milling is equal to the radius of the osteochondral junction at the level of the trochlear bone bed of the humeral condyle. Milling of bone in the lateral compartment removes the cartilage and bone of the trochlear notch and lateral coronoid of the ulna, the radial head cartilage and bone, and the articular cartilage and subchondral bone of the lateral condyle laterally to the level of the lateral bone surface of the intracondylar fossa. The lateral epicondyle and lateral condylar bone are left intact. Preferably, the mill tool 117 has a central conical section. The central conical section leaves a conical portion 116 of the bone, which coincides with the conical portion of the lateral humeral component 119. Additionally, the outer edge of the milling tool 117 also has a conical section. This coincides with the angled portion 115 of the radius head for attachment of the radial component 121.

After milling of the lateral compartment 114, the guide pin 102 is removed. All pins going into the humerus, radius and ulna are released from the sagittal fixation pin clamps. The elbow joint can now be opened for implantation of the radial component 121, the lateral ulnar component 118, and the lateral humeral component 119 (with the lateral polyethylene ring 120 attached). Since precision bone milling has already been accurately performed, opening of the elbow joint for insertion of the prosthesis components does not change the geometry. The radial component 121 is first inserted into milled bone bed. The lateral surface of the component is compressed against the flat lateral milled surface of the bone. The lower convex arc of the implant has an exact match to the precision milled concave arc 115 of the proximal radius bone bed. The center screw of the radial component is then drilled and inserted. The metal radial head meniscus insert is snapped into the radial component. Next, the lateral ulnar component 118 is pressed into its precision milled bone bed. The compression screws are drilled, measured, and inserted into the lateral ulnar component and underlying bone bed. The lateral humeral component 119 is then pressed and lightly tapped onto the bone bed of the lateral condyle with an orthopedic mallet. The prosthetic joint surfaces are reduced and the medial components are implanted in the same manner as the partial elbow arthroplasty described above. The medial condylar osteotomy is then repaired in the manner described above.

Having disclosed at least one embodiment of the present invention, various adaptations, modifications, additions, and improvements will be readily apparent to those of ordinary skill in the art. Such adaptations, modifications, additions and improvements are considered part of the invention which is only limited by the several claims attached hereto.

The invention claimed is:

1. A modular elbow joint prosthesis comprising:
a cylindrical medial humeral component having an axial hole therethrough, the medial humeral component comprising a central portion of a first diameter and end plates on either end of the central portion of greater diameter than the central portion;
a medial polyethylene ring, having an inner diameter corresponding to the first diameter, positioned around the central portion of the medial humeral component; and
a semicircular medial ulnar component surrounding a portion of the medial polyethylene ring, wherein the semicircular medial ulnar component comprises two countersunk screw holes.

2. The modular elbow joint prosthesis of claim 1, wherein the medial polyethylene ring has an outer conical surface, and the medial ulnar component has an inner conical surface.

3. The modular elbow joint prosthesis of claim 2, wherein the end plates of the medial humeral component have different diameters.

4. The modular elbow joint prosthesis of claim 1, further comprising a transcondylar bone screw within the axial hole of the medial humeral component.

5. The modular elbow joint prosthesis of claim 1, further comprising:
a cylindrical lateral humeral component having an axial hole therethrough, the lateral humeral component comprising a central portion of a second diameter and end plates on either end of the central portion of greater diameter than the central portion;
a lateral polyethylene ring, having an inner diameter corresponding to the second diameter, positioned around the central portion of the lateral humeral component;
a semicircular lateral ulnar component surrounding a portion of the lateral polyethylene ring; and
a radial component abutting the lateral polyethylene ring.

6. The modular elbow joint prosthesis of claim 5, wherein the lateral polyethylene ring has an outer surface which is barrel shaped and the lateral ulnar component has a concave inner surface.

7. The modular elbow joint prosthesis of claim 6, wherein the radial component has a concave upper surface.

8. The modular elbow joint prosthesis of claim 5, further comprising a transcondylar bone screw within the axial hole of the medial humeral component and the axial hole of the lateral humeral component.

9. The modular elbow joint prosthesis of claim 5, wherein one of the end plates of the medial humeral component has ridges thereon, and wherein one of the end plates of the lateral humeral component has ridges thereon, such that the ridges on the medial humeral component mate with the ridges on the lateral humeral component.

10. A surgical process for implanting the prosthesis of claim 1 in an elbow, the process comprising the steps of:
performing a sagittal osteotomy to remove at least a portion of the medial epicondyle;
removing a portion of the medial ulna and humeral condylar bone to the level of the central trochlea thereby generating a bone bed in the elbow;
inserting the prosthesis into the bone bed; and
reattaching the medial epicondyle.

11. The surgical process of claim 10, wherein the inserting step includes: attaching the humeral component of the prosthesis to the humeral condylar bone; and attaching the humeral component of the prosthesis to the medial ulna.

12. The surgical process of claim 10, further comprising the steps of:
removing a portion of the trochlear notch and lateral coronoid of the ulna, the radial head, and the subchondral bone of the lateral condyle; and
inserting a second prosthesis into the elbow where the portion of the trochlear notch and lateral coronoid of the ulna, the radial head, and the subchondral bone have been removed.

13. The surgical process of claim 10, further comprising the step of determining the sagittal plane of the elbow, wherein the sagittal osteomtomy is performed parallel to the determined sagittal plane, and the removing step removes bone perpendicular to the determined sagittal plane.

* * * * *